United States Patent [19]
Blake et al.

[11] Patent Number: 5,491,738
[45] Date of Patent: Feb. 13, 1996

[54] X-RAY DIFFRACTION APPARATUS

[75] Inventors: David F. Blake, Redwood City; Charles Bryson, Santa Clara; Friedemann Freund, San Francisco, all of Calif.

[73] Assignee: The United States of America as represented by the Administrator of the National Aeronautics and Space Administration, Washington, D.C.

[21] Appl. No.: 33,306

[22] Filed: Mar. 15, 1993

[51] Int. Cl.[6] .................................................. G01N 23/20
[52] U.S. Cl. ............................... 378/71; 378/49; 378/82; 378/90
[58] Field of Search .................. 378/71, 72, 73, 378/86, 82, 83, 88, 90, 45, 44, 46, 49; 250/370.09

[56] References Cited

U.S. PATENT DOCUMENTS

| | | | |
|---|---|---|---|
| 4,245,158 | 1/1987 | Burstein et al. | 250/370.09 |
| 4,955,974 | 9/1990 | Rhodes et al. | 378/36 |

OTHER PUBLICATIONS

Janesick, J. R., et al., "Present and Future CCDs For UV and X-Ray Scientific Measurements," *IEEE Trans. NS–32* 1(409):1–8 (1985).

Janesick, J. R., et al., "Charge–coupled device advances for x–ray scientific applications in 1986," *Optical Engineer.* 26(2):156–166 (1987).

Lumb, D. H., "Calibration and X–Ray Spectroscopy with Silicon CCSs," *Nucl. Instr. Meth. Phys. Res.* A290:559–564 (1990).

Luppino, G. A., et al., "Imaging and Nondispersive spectroscopy of soft x rays using a laboratory x–ray charge–coupled–device system," *Optical Engineer.* 26(10):1048–1054 (1987).

*Primary Examiner*—David P. Porta
*Attorney, Agent, or Firm*—Kenneth L. Warsh; Guy M. Miller; John G. Mannix

[57] ABSTRACT

An x-ray diffraction apparatus for use in analyzing the x-ray diffraction pattern of a sample. The apparatus includes a beam source for generating a collimated x-ray beam having one or more discrete x-ray energies, a holder for holding the sample to be analyzed in the path of the beam, and a charge-coupled device having an array of pixels for detecting, in one or more selected photon energy ranges, x-ray diffraction photons produced by irradiating such a sample with said beam. The CCD is coupled to an output unit which receives input information relating to the energies of photons striking each pixel in the CCD, and constructs the diffraction pattern of photons within a selected energy range striking the CCD.

6 Claims, 1 Drawing Sheet

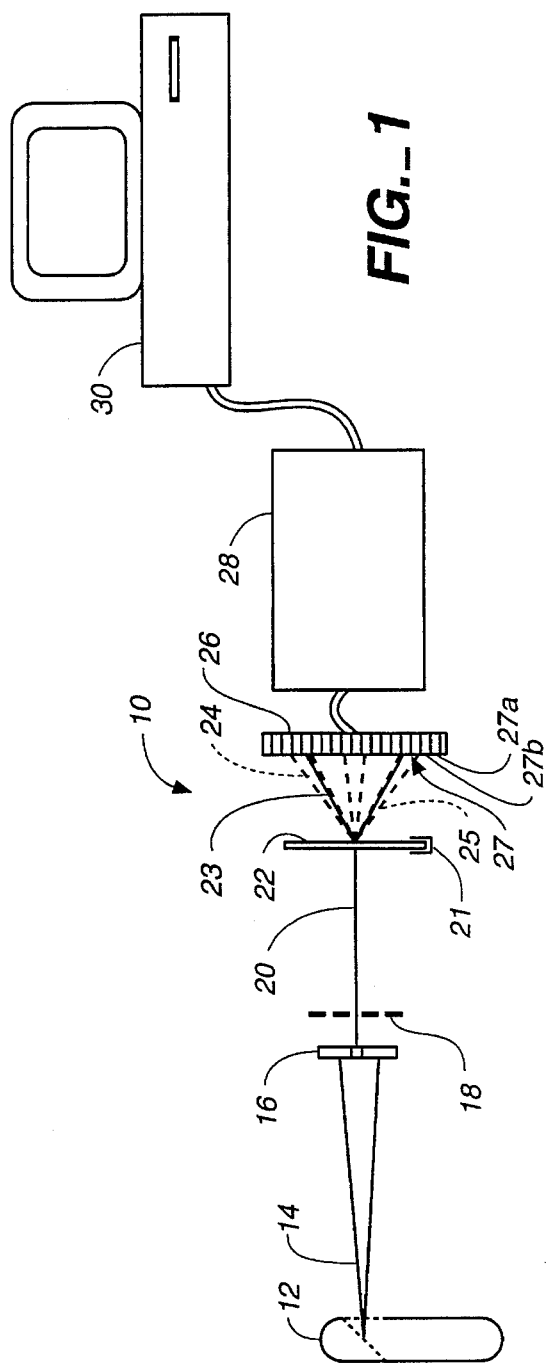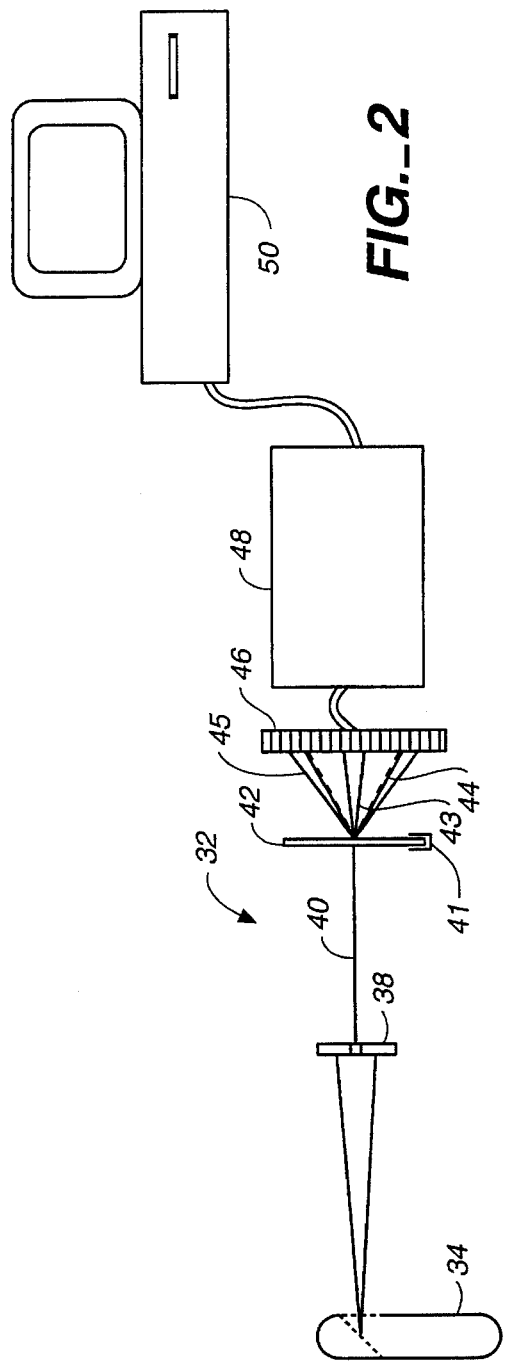

ized device", 6 :

X-RAY DIFFRACTION APPARATUS

FIELD OF THE INVENTION

The present invention relates to a x-ray diffraction device, and more specifically to a device with energy discrimination based on a CCD (charge-coupled device) array.

REFERENCES

Blake, D. F., et al., Lunar and Planetary Science XXIII:117 (1992).

Janesick, J. R., et al., IEEE Transactions NS-32(1):409 (1985a).

Janesick, J. R., et al., Rev. Sci. Instr. 56(5):796 (1985b).

Janesick, J. R., et al., Optical Engineering 26(2):156 (1987).

Lumb, D. H., "Calibration and X-Ray Spectroscopy with Silicon CDDs" in Nuclear Instruments and Methods in physics Research, A290, p. 559 (1990).

Luppino, G. A., et al., Optical Engineering 26(10):1048 (1987).

Marsh, K., et al., Rev. Sci. Instrum. 56(5):837 (1985).

Stern, R. A., et al., Rev. Sci. Instrum. 54(2):199 (1983) .

Toothacker, W. S., et al., "Radioisotopes as zero power sources of X-rays for X-ray diffraction analysis" in *Nucleonics in Aerospace* (Instrument Society of America) p. 341 (1968).

Vaniman, D. T., et al., Lunar and Planet Sci. XXII:1429 (1991a).

Vaniman, D. T., et al., Clay Min. Soc. 28th Ann. Mtg., p. 157 (1991b).

BACKGROUND OF THE INVENTION

This invention relates to certain aspects of the design of an instrument having a combined and concurrent capability for X-ray diffraction (XRD) with energy-discrimination, and X-ray fluorescence (XRF).

X-ray diffraction is a technique in which a collimated beam of X-rays is directed at a sample of unknown material. The angles of beams of X-rays diffracted from the sample are measured and the interplanar spacings of crystalline materials are determined using Bragg's law, $n\lambda=2d\sin\Theta$, where $\lambda$ is the wavelength of the X-radiation, d is the interplanar spacing within the crystal, and $\Theta$ is the quarter-angle of the cone of diffracted beams emanating from the sample. The resulting list of d-values (interplanar spacings) and diffracted intensities can be compared to equivalent listings from standards (published in computerized data bases such as the PCPDS powder diffraction file) to provide a definitive identification.

When a primary-beam X-ray photon strikes the sample, a variety of other interactions may take place in addition to simple Bragg diffraction. Photon-specimen interactions in which some energy is lost by the X-ray photon result in secondary signals which contain information about sample atoms. For example, X-ray photons can ionize sample atoms by removing inner shell electrons. The resulting inner shell vacancies are filled by electrons from outer shells of the same sample atom, and the difference in energy between the two orbitals is manifested as either an X-ray photon (secondary X-ray) or an Auger electron. The energies of secondary X-rays are characteristic of the elements from which they are emitted, and the number of X-rays and their energies can be translated into major, minor and trace element abundances. This interaction is called secondary X-ray Fluorescence (XRF), and there are known laboratory devices available for XRF analysis.

Commercially available XRD devices to date have not incorporated an XRF capability because of the many compromises which would have to be made for each device to function efficiently under operating conditions common to both. In the laboratory, XRD and XRF data are commonly used together to identify unknown minerals and compounds, but the data are gathered on two separate, large machines.

SUMMARY OF THE INVENTION

The present invention includes an x-ray diffraction apparatus for use in analysing the x-ray diffraction pattern of a sample. The apparatus includes a beam source for generating a collimated x-ray beam having one or more discrete x-ray energies, a holder for holding the sample to be analysed in the path of the beam, and a charge-coupled device having a *2-dimensional array of pixels for detecting, in one or more selected photon energy ranges, diffracted x-ray photons produced by irradiating such a sample with said beam. The CCD is coupled to an output unit which receives input information relating to the energies of photons striking each pixel in the CCD, and constructs the diffraction pattern of photons within a selected energy range striking the CCD.

In one embodiment, for use in discriminating a sample diffraction pattern from fluorescence emission from the sample, the beam source includes a filter effective to produce a monochromatic x-ray beam, and the CCD is designed to detect diffracted x-ray photons within the energy range of the beam, and exclude photons corresponding in energy to fluorescence emission from the sample.

In another embodiment, for use in analysing both the x-ray diffraction pattern and x-ray fluorescence spectrum of a sample, the beam source includes a filter effective to produce a monochromatic x-ray beam, and the CCD device is designed to detect and discriminate diffracted photons within the energy range of the beam (which constitute the diffraction pattern), and photons corresponding in energy to fluorescence emission from the sample.

In yet another embodiment, for use in analysing the fluorescence emission spectrum of the sample, when irradiated with a monochromatic beam of a selected energy, the beam source includes a filter effective to produce a monochromatic x-ray beam of the selected energy, and the CCD is designed to exclude diffraction-pattern photons within the energy range of the beam, and measure photons corresponding in energy to fluorescence emission from the sample.

In another general embodiment, the beam source is designed to produce multiple x-ray energies in the beam. The charge-coupled device is designed to measure the distribution of x-ray diffraction photons within one selected energy range, or within two or more selected energy ranges.

These and other objects and features of the invention will become more fully apparent when the following detailed description of the invention is read in conjunction with the accompanying drawings.

BRIEF DESCRIPTION OF THE DRAWINGS

FIG. 1 is a schematic representation of an x-ray apparatus constructed according to the present invention, and designed for analysing x-ray diffraction or fluorescence emission photons generated by a monochromatic beam; and FIG. 2 is a schematic representation of an x-ray apparatus constructed according to the present invention, and designed for analysing x-ray diffraction photons having different selected energies.

DETAILED DESCRIPTION OF THE INVENTION

FIG. 1 shows, in schematic representation, an x-ray diffraction apparatus 10 designed for analysing x-ray diffraction pattern(s) from a sample, such as shown at 22. The apparatus includes a conventional x-ray emitter 12, preferably one designed to produce a number of x-ray energies, such as corresponding to $CuK_a$. The noncollimated beam produced by the emitter is shown at 14. Beam 14 is passed through a collimator 16, and the collimated beam is further passed through a filter 18 to produce a collimated monochromatic beam 20. The filter is designed to remove all but a selected x-ray energy, e.g., the energy corrsponding to the $CuK_a$ line. Emitter 12, collimator 16 and filter 18 are referred to collectively herein as a source for producing a collimated, monochromatic x-ray beam, i.e., beam 20.

The sample to be analysed, indicated at 22, is supported in a sample holder 21 in the apparatus. The sample may be any sample suitable for x-ray diffraction studies, with the requirement that the sample thickness allows production of diffracted x-ray photons at the back side of the sample, when the sample is irradiated with beam 20, as indicated. In the figure, the solid-line cone indicated at 23 represents primary diffraction photons, and the dotted lines, such as lines 25, represent secondary emisssion produced by fluorescence emission from the sample, with irradiation by the collimated beam.

According to an important feature of the invention, the diffraction and fluorescence photons produced by irradiation of the sample are directed onto the face of a charge-coupled device (CCD) 26. The CCD contains a 2-dimensional planar array 27 of pixels, such as pixels 27a, 27b seen in one row of the array. The CCD is an array detector which is sensitive to X-ray photons, and which can record the energy of individual X-rays when operated in single-photon counting mode (see, for example, Luppino, et al., 1987; Stern, et al., 1983; Janesick, et al., 1985a,b, 1987; Marsh, et al., 1985; and Lumb, 1990). Typically, modern CCD array detectors rival traditional Si(Li) detectors with regard to energy resolution and sensitivity in the energy range of 0.2 to 10 KeV.

One preferred CCD is a TK512-B CCD from Tektronic (Beaverton, Oreg.). According to conventional CCD operation, the CCD can be selected to measure photons within a selected energy range, e.g., in the range of 8 KeV. Further, the array can be interogated at rapid intervals so that in successive intervals, the array reports the energy deposited by individual x-ray photons at single pixels of the array.

Also forming part of the invention is a controller unit 28 which receives input signals from each of the pixels in the CCD, relating to the pixel position and photon energy measured at each pixel, for use in constructing the diffraction pattern of photons within a selected energy range striking the array. The controller unit can be readily constructed for receiving and processing input from the CCD, according to well-known principles. Also included in the apparatus is a microprocessor 30 which can be used to provide a screen display for the controller unit and from which the CCD settings can be controlled by the user. The reporting unit and microprocessor are also referred to herein as reporting means.

FIG. 2 shows an x-ray diffraction apparatus constructed according to a second embodiment of the invention. The apparatus differs from device 10 only in the x-ray source, which in this embodiment is designed to produce a collimated x-ray beam 40 containing multiple x-ray lines, or energies. The source includes an emitter 34 like emitter 12, and a collimator 38 like collimator 16, but no wavelength filter.

The sample, such as sample 42, is designed to be held in a sample-holder 41, with primary and secondary x-rays produced by irradiation of the sample being directed onto the pixel array of a CCD 46 like CCD 26. The figure shows three different difraction cones 43, 44, and 45 which are due to diffraction from different-energy x-rays in the beam. Secondary event photons from sample fluorecence are not shown in the figure.

Below are described five embodiments of X-ray sources and position-sensitive, energy-discriminating X-ray detectors which have utility for different types of data collection.
1. The X-ray beam is monochromatic (monoenergetic) and only the diffraction pattern is of interest.

This is the most typical case in XRD applications, and is carried out by the embodiment shown in FIG. 1 in which the energy range for x-ray detection is selected to include the energy range of the monochromatic beam, and to exclude lower energy ranges, such as would correspond to secondary event x-rays i.e., all X-rays which suffer energy losses within the sample (those absorbed and reemitted as secondary fluorescence X-rays). This allows removal of "background" photon counts due to inelastic collisions within the sample.

An example of utility is the case of an iron-containing sample analyzed using $CuK\alpha$ X-radiation. The K shell absorption edge for Fe lies just below the $CuK\alpha$ energy, and $FeK\alpha$ X-rays are therefore strongly fluoresced by the primary beam. The result is a high X-ray background containing no diffraction information, which is emitted from the sample isotropically. The CCD allows the removal of background counts as they are detected.
2. The X-ray beam is monochromatic and both the X-ray diffraction information and secondary X-ray fluorescence information is of interest.

In this application, the FIG. 1 embodiment is operated in a mode where both the energies of the diffracted x-rays and expected fluorescent emission x-rays are recorded by the CCD. Thus both X-ray fluorescence and X-ray diffraction information is collected concurrently by the same detector. The diffraction pattern consists of an image made of all X-rays having the energy of the primary beam, and an X-ray fluorescence analysis consists of all X-rays which have energies less than the primary beam energy. Secondary fluorescence X-rays are summed into a histogram (an energy-dispersive X-ray spectrum) which can be used to identify the major, minor, and trace element composition of the sample.

A combined XRD/XRF device, providing both crystallographic and elemental information from the sample material, can yield definitive phase identifications even from complex mixtures of materials. An XRF device by itself would be unable to distinguish iron and magnesium oxides from hydroxides Likewise, clay minerals would be indistinguishable from amorphous materials or poorly crystalline hydroxides. With diffraction results from an XRD and elemental data obtained by XRF, distinguishing such differences in mineralogy is straightforward.
3. The X-ray beam is preferably monochrmoatic, and only the X-ray fluorescence spectrum is of interest.

In this application, the apparatus of FIG. 1 is operated in a mode in which the CCD measures x-rays in the energy ranges correponding to secondary-event x-rays due to expected fluorescence energy of the sample, but excludes energy ranges corresponding to the beam energy. That is, the apparatus is functioning only to measure fluorescence emission from the sample.

Present applications such as dedicated X-ray fluorescence analyzers, and X-ray analysis systems attached to electron microscopes use monolithic energy-dispersive detectors or wavelength-dispersive crystals. In all of the detectors, X-rays are detected and processed in serial fashion; one photon at a time. In a position-sensitive, energy-dispersive detector, X-rays are detected in parallel fashion with each pixel of the CCD array acting as an energy-dispersive detector. The disadvantage of CCD X-ray detectors is that only one X-ray can be detected per pixel between array readouts (this is called single photon counting mode). Should more than one X-ray be detected in a single pixel between readouts, the charge pulses will sum and the measurement of the X-ray energy will be incorrect.

There are two advantages of CCD X-ray detectors over the conventional monolithic detectors. First, the "noise floor" or dark current in CCDs is much lower than in conventional detectors. This permits operation in the very low energy region of the X-ray spectrum, allowing the detection of lithium and beryllium X-rays and the high efficiency detection of carbon, nitrogen, oxygen and the like. As a corollary to this, CCD detectors can operate at temperatures in the −50° C. to −70° C. temperature range. Conventional detectors must be cooled to liquid nitrogen temperatures (−200° C.). Secondly, defects in the high purity silicon used in monolithic detectors limit the energy resolution of X-ray peaks. In CCDs, a volume the size of a single pixel (25×25×10 micrometers) can be defect free, resulting in much greater energy resolution.

4. The X-ray beam is not monochromatic and only a particular diffraction pattern is interest.

In this application, the embodiment in FIG. 2 is operated in a mode in which the CCD detects diffracted x-rays corresponding to one or more beam energies, but excludes energy ranges corresponding to fluorescence x-rays produced by the beam in the sample.

In one particular embodiment, a conventional X-ray tube source is used to provide unfiltered X-radiation (characteristic and Bremstrahhlung X-rays) to the sample. The CCD detector is used to detect all X-rays scattered by the sample and a computer algorithm is used to reject those X-rays which have energies different from the characteristic X-radiation of the source. In similar fashion, a "white" X-ray source (containing all wavelengths) could be used as a photon source for diffraction, and a CCD detector could be used to select a particular wavelength (energy) for the diffraction experiment.

This configuration is useful for diffraction experiments in which the diffracted X-ray energy is finely tuned to avoid strong absorption in the sample.

5. In the case where a radiation source is used (synchrotron radiation, for example) and only the diffraction pattern is of interest.

In this application, the embodiment in FIG. 2 is operated in a mode in which the CCD is detecting diffracted x-rays correponding to a selected beam energies, but excludes energy ranges corresponding to fluorescence x-rays produced by the beam in the sample.

A diffraction experiment is performed in which the detector records the position and energy of every X-ray which interacts with the sample. Using Bragg's law, the interplanar spacings of a crystaline sample can be determined from the diffraction angle and the energy (wavelength) and location of each X-ray. Thus, a particular set of atomic planes in the sample will diffract X-rays of different wavelengths (energies) to different locations on the detector. The d-value of this particular set of planes could be calculated by solving the Bragg equation for each X-ray's position and energy.

Although the invention has been described with respect to specific embodiments and applications, it will be appreciated that various changes and modification can be made without departing from the invention.

It is claimed:

1. X-ray diffraction apparatus for use in analysing the x-ray diffraction pattern of a sample, consisting essentially of, a beam source for generating a collimated x-ray beam having one or more discrete x-ray energies, a holder for holding the sample to be analysed in the path of said beam, a charge-coupled device having a 2-dimensional array of pixels for detecting, in one or more selected photon energy ranges, x-ray diffraction photons produced by irradiating such a sample with said beam, and means coupled to said charge-coupled device for receiving input information relating to the energies of photons striking each pixel in said device, for use in reporting the diffraction pattern of photons within a selected energy range striking said device.

2. The apparatus of claim 1, for use in discriminating a sample diffraction pattern from fluorescence emission from the sample, wherein said beam source includes a filter effective to produce a monochromatic x-ray beam, and said charge-coupled device is operated to detect diffraction-pattern photons within the energy range of the beam, and exclude photons corresponding in energy to fluorescence emission from the sample.

3. The apparatus of claim 1, for use in analysing both the x-ray diffraction pattern and x-ray fluorescence spectrum of a sample, wherein said beam source includes a filter effective to produce a monochromatic x-ray beam, and said charge-couple device is operated to detect and discriminate diffracted-pattern photons within the energy range of the beam, and photons corresponding in energy to fluorescence emission from the sample, for use in constructing an x-ray diffraction pattern and for measuring total fluorescence emission from the sample.

4. The apparatus of claim 1, for use in analysing the fluorescence emission of the sample, when irradiated with a monochromatic beam of a selected energy, wherein said beam source includes a filter effective to produce a monochromatic x-ray beam of the selected energy, and said charge-coupled device is operated to exclude diffraction-pattern photons within the energy range of the beam, and measure photons corresponding in energy to fluorescence emission from the sample.

5. X-ray diffraction apparatus for use in analyzing the x-ray diffraction pattern of a sample, comprising a beam source for generating a collimated x-ray beam having one or more discrete x-ray energies, wherein said beam is designed to produce multiple x-ray energies in the beam, a holder for holding the sample to be analyzed in the path of said beam, a charge-coupled device having a 2-dimensional array of pixels for detecting, in one or more selected photon energy ranges, x-ray diffraction photons produced by irradiating such a sample with said beam, wherein said charge-coupled device is operated to measure the distribution of x-ray diffraction photons within one selected energy range, and means coupled to said charge-coupled device for receiving input information relating to the energies of photons striking each pixel in said device, for use in reporting the diffraction pattern of photons within a selected energy range striking said device.

6. X-ray diffraction apparatus for use in analyzing the x-ray diffraction pattern of a sample, comprising a beam source for generating a collimated x-ray beam having one or more discrete x-ray energies, wherein said beam is designed to produce multiple x-ray energies in the beam, a holder for holding the sample to be analyzed in the path of said beam, a charge-coupled device having a 2-dimensional array of pixels for detecting, in one or more selected photon energy ranges, x-ray diffraction photons produced by irradiating such a sample with said beam, wherein said charge-coupled device is operated to measure the distributions of x-ray diffraction photons within two or more selected energy ranges and means coupled to said charge-coupled device for receiving input information relating to the energies of photons striking each pixel in said device, for use in reporting the diffraction pattern of photons within a selected energy range striking said device.

\* \* \* \* \*